(12) United States Patent
Tumey

(10) Patent No.: US 11,382,799 B2
(45) Date of Patent: Jul. 12, 2022

(54) TAMPON WITH INTRAVAGINAL CANNABINOID DELIVERY DEVICE

(71) Applicant: David M. Tumey, Coral Springs, FL (US)

(72) Inventor: David M. Tumey, Coral Springs, FL (US)

(73) Assignee: BLUEGRASS FARMACEUTICALS, LLC, Belton, KY (US)

( * ) Notice: Subject to any disclaimer, the term of this patent is extended or adjusted under 35 U.S.C. 154(b) by 474 days.

(21) Appl. No.: 16/675,346

(22) Filed: Nov. 6, 2019

(65) Prior Publication Data

US 2020/0163807 A1 May 28, 2020

Related U.S. Application Data

(60) Provisional application No. 62/771,329, filed on Nov. 26, 2018.

(51) Int. Cl.
| | |
|---|---|
| *A61K 31/335* | (2006.01) |
| *A61K 9/00* | (2006.01) |
| *A61F 13/20* | (2006.01) |
| *A61M 31/00* | (2006.01) |
| *A61K 36/185* | (2006.01) |
| *A61F 13/26* | (2006.01) |

(52) U.S. Cl.
CPC ........ *A61F 13/2074* (2013.01); *A61F 13/266* (2013.01); *A61K 9/0036* (2013.01); *A61K 36/185* (2013.01); *A61M 31/002* (2013.01)

(58) Field of Classification Search
CPC ............................ A61K 31/335; A61K 9/0036
USPC .......................................... 514/455; 424/431
See application file for complete search history.

(56) References Cited

U.S. PATENT DOCUMENTS

| | | | |
|---|---|---|---|
| 2,739,593 | A | 3/1956 | McLaughlin |
| 3,884,233 | A | 5/1975 | Summey |
| 4,318,405 | A | 3/1982 | Sneider |
| 4,340,055 | A | 7/1982 | Sneider |
| 6,086,909 | A | 7/2000 | Harrison |
| 6,197,327 | B1 | 3/2001 | Harrison |
| 6,207,696 | B1 | 3/2001 | Peterson |
| 6,416,779 | B1 | 7/2002 | D'Augustine |
| 6,512,874 | B2 | 6/2003 | Harrison |
| 6,982,091 | B2 | 1/2006 | Pauletti |
| 7,004,171 | B2 | 2/2006 | Benita |
| 7,344,732 | B2 | 3/2008 | Gehling |
| 7,527,614 | B2 | 5/2009 | Heuer |
| 7,774,556 | B2 | 8/2010 | Karamcheti et al. |
| 7,993,667 | B2 | 8/2011 | Gehling |
| 8,137,327 | B2 | 3/2012 | Sokal |
| 8,388,996 | B2 | 3/2013 | Gehling |
| 8,404,272 | B2 | 3/2013 | Shalaby |
| 9,370,574 | B2 | 6/2016 | Shalaby |
| 10,092,538 | B2 | 4/2018 | Changoer |

*Primary Examiner* — Raymond J Henley, III
(74) *Attorney, Agent, or Firm* — A Patent Lawyer, LLC; R. William Graham

(57) ABSTRACT

A tampon and therapeutic delivery device is disclosed and includes a generally cylindrical applicator tube defining a cartridge within which a tampon is slidably received for ejection through one end of the cartridge. A generally hollow cylindrical plunger member is slidably received within an opposite end of the cartridge for ejecting the tampon therefrom. A cannabinoid-infused disintegrable carrier material is partially embedded in and movably held by the tampon for intravaginal delivery when ejected from the cartridge, whereupon the cannabinoid agent is released into the vagina and absorbed through the vaginal mucosa to provide relief of dysmenorrhea. The cartridge has a plurality of slots to permit pre-lubrication of the tampon, if desired, prior to insertion into the vaginal cavity. The system delivers a higher concentration to the muscle of the uterus, the primary site for the dyskinetic muscle contraction, which is the pathophysiologic cause of dysmenorrhea.

8 Claims, 2 Drawing Sheets

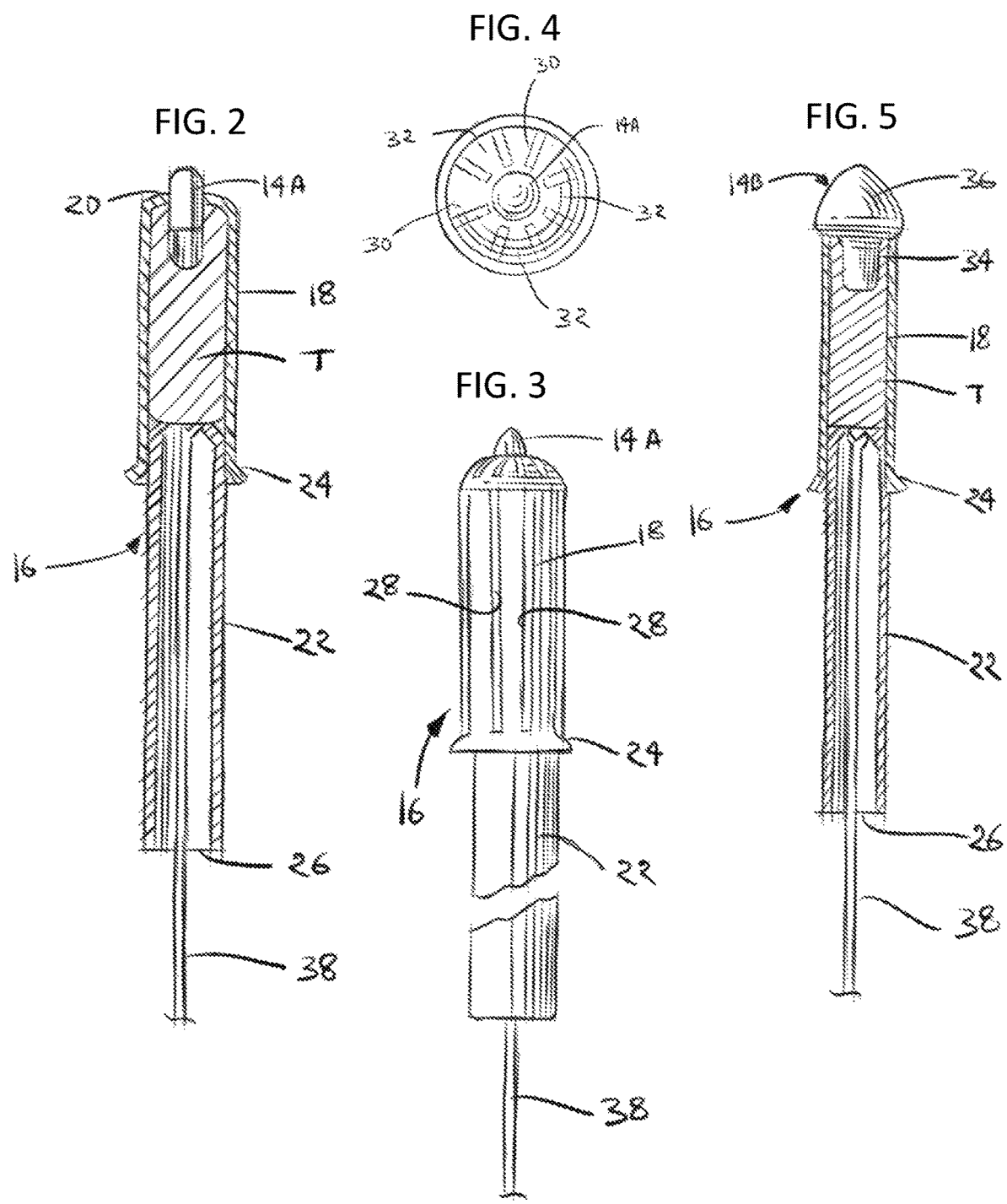

TAMPON WITH INTRAVAGINAL CANNABINOID DELIVERY DEVICE

FIELD OF THE INVENTION

The present general inventive concept concerns devices, methods, and compositions for treating dysmenorrhea by intravaginal administration of therapeutic cannabinoids to the vaginal mucosal lining and uterus.

BACKGROUND OF THE INVENTION

The present general inventive concept relates to a tampon and therapeutic cannabinoid delivery device or combination, and particularly to a tampon in a form which carries a cannabinoid into vaginal cavities or the like.

Medicated vaginal tampons and tampon and suppository combinations are known for delivering medicaments or drugs into vaginal cavities for various reasons such as contraception, hygienic or health-related purposes. In some instances, the tampon itself is impregnated with a particular solution or active ingredient. In other instances, it has become desirable to provide a means for delivering a drug into the vaginal cavity in the form of an encapsulate or molded spheroid.

One of the problems with the utilization of capsulelike medicaments is that it is very difficult to properly locate and position the capsule for its intended purpose, because of the natural tendencies of the vagina to flush or reject any foreign body. The use of capsule-loaded tampons has been attempted, but, although the tampon is useful for initial insertion of the capsule, prior tampons utilized for these purposes could not properly place and maintain the capsule in the desired position within the vaginal cavity.

U.S. Pat. No. 6,197,327 to Harrison, et al., dated Mar. 6, 2001, describes a drug delivery system explicitly for the treatment of dysmenorrhea. The patent relates myriad drug delivery methods and techniques including a tampon-like device, vaginal ring, pessary, tablet, vaginal sponge, suppository, bioadhesive tablet, bioadhesive microparticle, lotion, cream, foam, ointment, paste, solution or gel. While the patent describes myriad methods for delivering medicaments to the vaginal mucosa, they all inherently lack the ability to precisely position a medicament within the vaginal cavity for optimal placement, delivery and uptake.

U.S. Pat. No. 2,739,593 to McLaughlin, dated Mar. 27, 1956, and U.S. Pat. No. 3,884,233 to Summey, dated May 20, 1975, disclose medicated vaginal tampons and/or tampon and suppository combinations which are intended to deliver a medicament or medicated suppository into the vaginal cavity. However, both of these patents illustrate the issues described above in properly inserting, positioning and maintaining an encapsulate or spheroid in a desired position within the vaginal cavity. In both of these patents, the tampon terminates well short of the end of the cartridge applicator to define a pocket for receiving the medicament or medicated suppository. Not only does this unduly lengthen the overall dimensions of the delivery devices, but once the medicament or suppository clears the pocket defined by the tampon cartridge, there is no control whatsoever of properly positioning the medicament or suppository within the vaginal cavity. With the natural vaginal rejecting tendencies, this is a serious limitation with such devices heretofore available. In fact, Summey shows a device which includes a separate container and cap for the suppository utilized therein.

Another problem in utilizing tampons for delivery of the capsules is the fact that the absorbent nature of the tampon itself actually inhibits the dissolving or disintegration of the capsule containing the desired therapeutic agent. More particularly, the particular therapeutic agent, in capsule form, is mixed with some carrier material that is gradually broken down by body fluids. In using a tampon to deliver the capsule, the tampon itself has a tendency to absorb the body fluids rather than permitting the fluids to dissolve the capsule. Some capsules utilize carrier materials which dissolve in response to body heat, but for encapsulated medicaments, it is generally undesirable to wait for this means to activate and dissolve the capsule, rather the faster and more effective activation means of utilizing body fluids.

The present general inventive concept is directed to fulfilling the aforementioned needs and solving the enumerated problems by providing a tampon with an integrated cannabinoid delivery device which has a more effective means for delivering a cannabinoid-infused disintegrable carrier into a vaginal cavity, or the like, and means for pre-lubricating the tampon and provide a more effective means for activating the same.

SUMMARY OF THE INVENTION

An object, therefore, of the present general inventive concept is to provide a new and improved, novel tampon and cannabinoid delivery device of the character described.

In the exemplary embodiment of the present general inventive concept, the tampon and cannabinoid delivery device includes a generally cylindrical inserter means, with a tampon slidably positioned within the inserter means for expulsion through the ejection end portion thereof. Ejection means is slidably received within an opposite end portion of the inserter means for ejecting the medicated tampon from said ejection end of the inserter means. A cannabinoid-infused disintegrable carrier material is at least partially embedded in and movably held by the tampon for intravaginal delivery into a vaginal cavity, or the like, by ejection from the inserter means and held in proper position within the vaginal cavity by the tampon whilst the carrier material dissolves.

In one form of the present general inventive concept, the cannabinoid-infused disintegrable carrier material is substantially embedded within the tampon generally centrally thereof at the end of the tampon adjacent said ejection end of the cylindrical inserter means. The ejection end of the inserter means closes over the peripheral edges of the tampon and is slotted to define generally triangular wedge-shaped segments which surround and engage portions of the cannabinoid delivery device protruding from the tampon.

In another form of the present general inventive concept, the cannabinoid-infused disintegrable carrier material is generally mushroom shaped with a stem portion embedded and held within the tampon, and a head portion overlying the ejection end of the tampon adjacent the forward end of the tubular inserter means.

As shown herein, the cylindrical inserter means is in the form of a round sheathing tube defining a hollow cartridge for receiving the tampon and associated medicaments. The ejecting means which is slidably received within the inserter means is in the form of a generally hollow cylindrical plunger member. In this form, a removal string is secured to the inner proximal end of the tampon within the cartridge and extends through the generally hollow plunger member at the end thereof opposite the cartridge.

A beneficial feature of the present general inventive concept is the provision of aperture means in the inserter means to permit pre-lubrication of the tampon prior to insertion into the vaginal cavity. In the exemplary embodiment of the inventive concept shown herein, the aperture means comprises a plurality of slotted fenestrations extending lengthwise of the inserter means or cartridge and along a substantial length of the tampon. In this manner, the tampon and cannabinoid delivery device of the present general inventive concept can be pre-lubricated, for example, with an aqueous-based lubricating solution, immediately prior to inserting the device into the vaginal cavity. The lubricating solution helps facilitate insertion and control the positioning of the cannabinoid-infused carrier material when deposited within the vaginal cavity.

It should be readily understood that the tampon and cannabinoid delivery device of the present general inventive concept has many additional functional applications beyond the treatment of dysmenorrhea, such as delivering contraceptives for prevention of pregnancy and antibiotics for prevention or treating of venereal disease. In addition, such materials and beneficial agents as lubricants, deodorants, medication, natural secretion replacement, and other like applications can be employed with the present general inventive concept where it is desirable to maintain a beneficial agent or substance in proper position within the vaginal cavity.

Other objects, features and advantages of the present general inventive concept will be apparent from the following description, the accompanying drawings and the appended claims.

BRIEF DESCRIPTION OF THE DRAWINGS

The following example embodiments are representative of exemplar techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be emphasized or exaggerated for clarity. A wide variety of additional embodiments will be more readily understood and appreciated through the following detailed description of the example embodiments, with reference to the accompanying drawings in which:

FIG. 2 is a longitudinal central sectional view through an inserter and ejecting means, with one form of cannabinoid carrying tampon of the present general inventive concept;

FIG. 3 is an elevational view of the device of FIG. 2, illustrating the slots in the inserter means for pre-lubrication of the tampon;

FIG. 4 is an end elevational view of the device of FIG. 2, illustrating the slotted triangularly shaped segments of the inserter means surrounding and engaging the cannabinoid delivery device; and FIG. 5 is a longitudinal central sectional view through an inserter and ejecting means, with another form of cannabinoid carrying tampon of the present general inventive concept.

DETAILED DESCRIPTION OF THE PREFERRED EMBODIMENT

Figure 1:
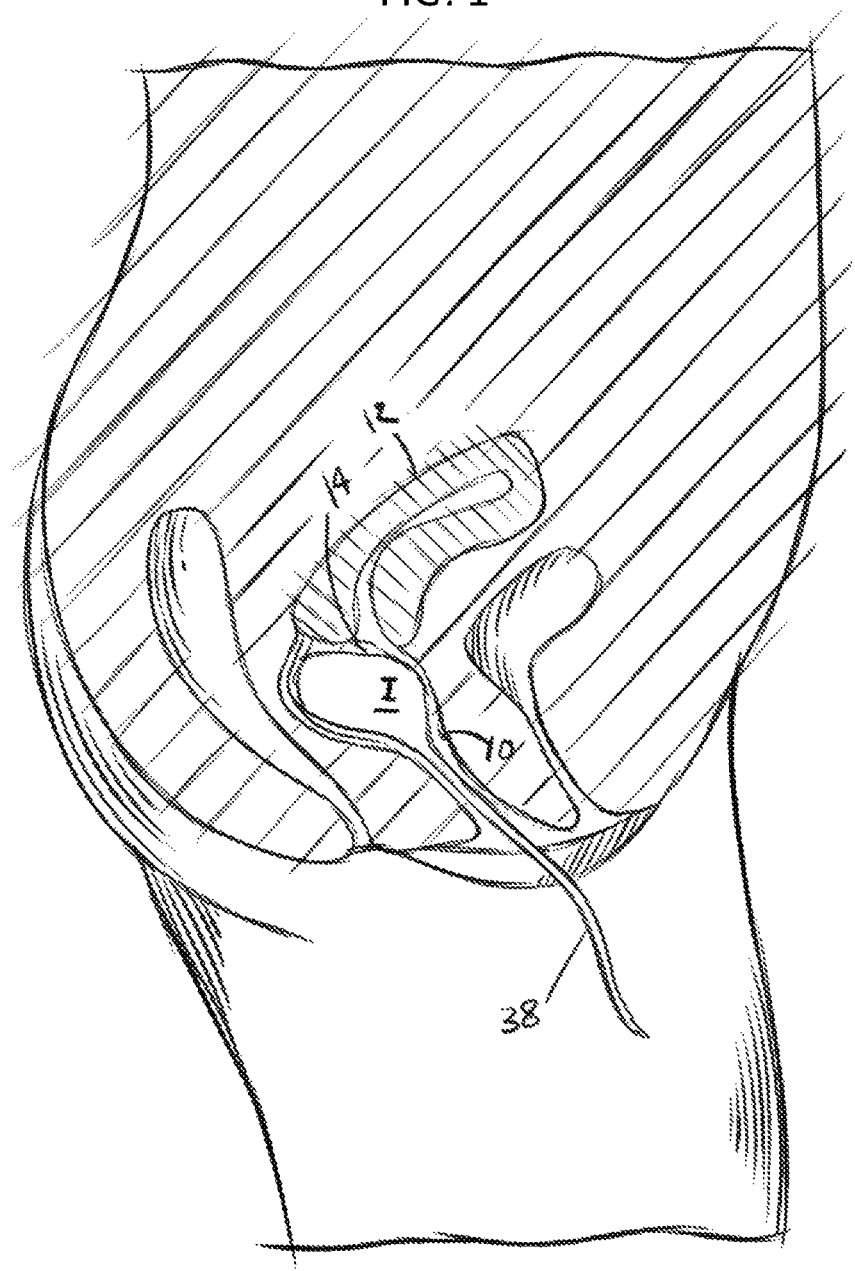
FIG. 1 is an anatomical diagram of a vaginal cavity, with a tampon and partially disintegrated cannabinoid delivery device properly positioned therein by the system of the present general inventive concept.

Referring to the drawings in greater detail, FIG. 1 is a female pelvic anatomy diagram illustrating a tampon T which has been inserted into a vaginal cavity 10. The tampon is expanded, and properly positioned adjacent the opening to uterus 12. A partially disintegrated cannabinoid delivery device 14 is shown properly inserted and positioned by the expanded tampon. This view illustrates the desired functioning of the device of the present general inventive concept, after use, as now will be described.

Referring to FIG. 2, a tampon and cannabinoid delivery device in accordance with the present general inventive concept is generally designated by the numeral 16. The device includes a generally cylindrical inserter means 18. The inserter means as shown is in the form of a round sheathing tube defining a cartridge for slidably receiving a tampon T for ejection through one end portion 20 of the cartridge.

Ejecting means 22, in the form of a generally hollow cylindrical plunger member, is slidably received within a tapered end 24 of cartridge 18 opposite end 20 of the cartridge. The ejecting plunger 22 engages the inner proximal end of tampon T for ejecting the tampon from end 20 of cartridge 18. The tapered end 24 of cartridge 18 provides a finger grasping portion to facilitate ejection of the tampon by means of an individual's thumb engaging the outer end 26 of plunger member 22.

A generally bullet-shaped spheroid 14A molded of cannabinoid-infused disintegrable carrier material is at least partially embedded within and movably held by tampon T for delivery into vaginal cavity 10 (FIG. 1) by ejection from cartridge 18 after the cartridge is inserted into the vaginal cavity.

In the form of the inventive concept shown in FIG. 2, carrier spheroid 14A is embedded and held within tampon T generally centrally thereof adjacent end 20 of cartridge 18. Normally, the density of the tampon would be sufficient for retaining and holding the carrier spheroid for proper insertion completely within the vaginal cavity as described in relation to FIG. 1. However, in some particular circumstances, or with certain tampon materials, it may be desirable to utilize a biocompatible adhering substance between the spheroid and tampon to facilitate proper and precise positioning of the carrier spheroid within the vaginal cavity.

Referring to FIG. 3, a beneficial feature of the present general inventive concept is the provision of features on cartridge 18 for facilitating pre-lubrication of tampon T prior to insertion into the vaginal cavity. More particularly, cartridge 18 is provided with aperture means in the form of a plurality of slotted fenestrations 28 through the sides thereof for pre-lubricating the tampon. The slotted fenestrations preferably extend lengthwise of the cartridge along a substantial length of the tampon to insure complete lubrication of the tampon. The tampon itself is fabricated of a compressed body of suitable soft, porous and absorbent material which expands appropriately within the vaginal cavity as shown in FIG. 1. This pre-lubrication feature of the present general inventive concept is also enhanced by the fact that the cannabinoid carrier spheroid is at least partially embedded within the tampon itself. In this manner, the embedded portion of the carrier spheroid is activated just as rapidly as the protruding portion which is activated primarily by body heat. The combination of the pre-lubricated tampon and body heat, promotes a rapid break-down of the carrier material for the cannabinoid-infused in the carrier material. Thus, it can be seen that the embedding of the carrier spheroid within the tampon provides a dual function of insuring proper positioning of the carrier spheroid within the vaginal cavity as well as combining with the pre-lubrication feature of the present general inventive concept to insure rapid and uniform dissolving of the carrier spheroid itself.

Referring to FIG. 4, it can be seen that the outer end of cartridge 18 closes over the peripheral edge of the tampon and is slotted, as at 30, to define generally triangular wedge-shaped segments 32 which surround and engage the portions of carrier spheroid 14A which protrude from the tampon. These triangular wedge-shaped segments also facilitate holding the carrier spheroid in proper position centrally embedded in the tampon.

Referring to FIG. 5, a modified form of cannabinoid-infused carrier, generally designated 14B, is shown. Except for the elimination of the closed end 20 of cartridge 18, the tampon and associated components are identical to the device shown in FIGS. 2 and 3 and like numerals have been applied.

Carrier spheroid 14B shown in FIG. 5 is generally mushroom shaped with a stem portion 34 embedded and held within tampon T, similarly to the description of carrier spheroid 14A, above. Carrier spheroid 14B includes an enlarged, rounded head portion 36 which protrudes radially outwardly and overlies both the end of tampon T and the open end of cartridge 18. Just as with the rounded end 20 and round carrier spheroid 14A in FIG. 2, the rounded head portion 36 of carrier spheroid 14B prevents any damage to the lining of the vaginal cavity and the uterus during insertion of the tampon and delivery device thereinto.

With both forms shown in FIGS. 2 and 5, a removal string 38 is secured at one end to the inner proximal end of tampon T and extends completely through the opposite end of the generally hollow ejecting plunger member 22. After the tampon and carrier spheroid are properly inserted into the vaginal cavity, cartridge 28 and plunger member 22 may be removed and discarded, leaving removal string 38 for subsequently removing the tampon after a prescribed period of time.

The above described embodiments are set forth by way of example and are not for the purpose of limiting the scope of the present general inventive concept. It will be readily apparent that obvious modifications, derivations and variations can be made to the embodiments without departing from the scope of the present general inventive concept. Accordingly, the claims appended hereto should be read in their full scope including any such modifications, derivations and variations.

What is claimed is:

1. A tampon and cannabinoid delivery device, which includes:
    an inserter, with a medicated tampon slidably positioned within said inserter for expulsion through an ejection end portion thereof;
    means for ejecting said medicated tampon from said ejection end of said inserter; and
    a cannabinoid-infused disintegrable carrier material at least partially embedded in and movably held by said tampon for intravaginal delivery into a vaginal cavity by ejection from the inserter and held in proper position within the vaginal cavity by said tampon whilst said carrier material dissolves.

2. The tampon and cannabinoid delivery device of claim 1, wherein said cannabinoid-infused disintegrable carrier material is substantially embedded within said tampon generally centrally therein at an end of said tampon adjacent said ejection end of said inserter.

3. The tampon and cannabinoid delivery device of claim 1, wherein said ejection end of said inserter surrounds peripheral edges of said tampon and is slotted to define segments which surround and engage portions of said cannabinoid delivery material protruding from the tampon.

4. The tampon and cannabinoid delivery device of claim 1, wherein said cannabinoid-infused disintegrable carrier material is generally mushroom shaped with a stem portion embedded and held within said tampon, and a head portion overlying said ejection end of said tampon adjacent a forward end of said inserter.

5. The tampon and cannabinoid delivery device of claim 1, wherein said inserter is a round sheathing tube defining a hollow cartridge for receiving said tampon and cannabinoid-infused disintegrable carrier material.

6. The tampon and cannabinoid delivery device of claim 5, wherein said means for ejecting is slidably received within said inserter is further characterized to include a generally hollow plunger member.

7. The tampon and cannabinoid delivery device of claim 6, wherein a removal string is secured to an inner proximal end of said tampon within said cartridge and extends through said generally hollow plunger member at said end opposite said cartridge.

8. The tampon and cannabinoid delivery device of claim 3, wherein said slotted segments comprises a plurality of slotted fenestrations extending lengthwise of said inserter a substantial length of said tampon.

\* \* \* \* \*